United States Patent
Pinski

(10) Patent No.: US 8,680,055 B2
(45) Date of Patent: Mar. 25, 2014

(54) METHODS FOR DECREASING STEROIDOGENESIS IN PROSTATE CANCER CELLS

(75) Inventor: Jacek Pinski, La Canada, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/376,131

(22) PCT Filed: Jun. 2, 2010

(86) PCT No.: PCT/US2010/037128
§ 371 (c)(1),
(2), (4) Date: Mar. 12, 2012

(87) PCT Pub. No.: WO2010/141630
PCT Pub. Date: Dec. 9, 2010

(65) Prior Publication Data
US 2012/0164136 A1 Jun. 28, 2012

Related U.S. Application Data

(60) Provisional application No. 61/183,911, filed on Jun. 3, 2009.

(51) Int. Cl.
*A61K 38/24* (2006.01)
*A61K 38/00* (2006.01)
*C07K 16/00* (2006.01)

(52) U.S. Cl.
USPC ............ 514/19.5; 514/10.1; 530/389.7

(58) Field of Classification Search
None
See application file for complete search history.

(56) References Cited

U.S. PATENT DOCUMENTS

| | | | |
|---|---|---|---|
| 2005/0042205 A1 | 2/2005 | Nikolics et al. | 429/93.2 |
| 2007/0015713 A1* | 1/2007 | Bowen et al. | 514/15 |

FOREIGN PATENT DOCUMENTS

| | | | | |
|---|---|---|---|---|
| WO | WO 2007/011434 A1 | 1/2007 | | |
| WO | WO2007011434 | * | 1/2007 | ............ A61K 38/09 |
| WO | WO 2010/096801 A1 | 8/2010 | | |

OTHER PUBLICATIONS

Leuschner et al., Targeted destruction of Androgen-sensitive and insensitive prostate cancer cells and xenografts through Luteinizing hormone receptors, Prostate, 46, 116-125, 2001.*
Dirnhofer et al. Coexpression of gonadotropic hormones and their corresponding FSH- and LH/CG-Receptors in the human prostate, The prostate, 35, 212-220, 1998.*
Pelletier et al. Cellular localization of mRNA expression of enzymes involved in the formation and inactivation of hormonal steroids in the mouse prostate. J. Histochem. Cytochem. 52, 1351-1356, 2004.*
Dillard et al. Androgen-independent prostate cancer cells acquire the complete steroidogenic potential of synthesizing testosterone from cholesterol. Mol. Cell. Endocrinol. 295, 115-120, 2008.*
G. Bodek et al., "Targeted Ablation of Prostate Carcinoma Cells, Through LH Receptor Using Hecate-CGβ Conjugate: Functional Characteristic and Molecular Mechanism of Cell Death Pathway", Experimental Biology and Medicine, vol. 230, No. 6, Jun. 2005, pp. 421-428.
Anonymous: News Release4 GTx reports fourth quarter and Year End 2007 results, Feb. 19, 2008.
R. B. Montgomery et al., "Maintenance of Intratumoral Androgens in Metastatic Prostate Cancer: A Mechanism for Castration-Resistant Tumor Growth", Cancer Research, vol. 68, No. 11, Jun. 1, 2008, pp. 4447-4454.
L. H. Heitman et al., "Substituted Terphenyl Compounds as the First Class of Low Molecular Weight Allosteric Inhibitors of the Luteinizing Hormone Receptor", Journal of Medicinal Chemistry, vol. 52, No. 7, Apr. 9, 2009, pp. 2036-2042.
International preliminary report on patentability dated Dec. 15, 2011 issued in corresponding PCT application PCT/US2010/037128.

* cited by examiner

*Primary Examiner* — Elly-Gerald Stoica
(74) *Attorney, Agent, or Firm* — DLA Piper LLP (US)

(57) ABSTRACT

The present invention discloses compositions and methods for treating diseases such as cancer by targeting luteinizing hormone (LH) or its receptor (LHR) involved in androgen synthesis or testosterone production.

7 Claims, 9 Drawing Sheets

*LNCaP Cells*

Negative Ctrl      LH      LHR

*PC-3 Cells*

Negative Ctrl      LH      LHR

METHODS FOR DECREASING STEROIDOGENESIS IN PROSTATE CANCER CELLS

CROSS-REFERENCE TO RELATED APPLICATIONS

This application claims the benefit of U.S. Provisional Application No. 61/183,991, filed Jun. 3, 2009, the entire contents of which are incorporated herein by reference.

FIELD OF THE INVENTION

The present invention relates in general to compositions and methods for treatment of cancer. More specifically, the invention provides compositions and methods for treating diseases such as cancer by disrupting the luteinizing hormone (LH)/luteinizing hormone receptor (LHR) signaling pathway in cancer cells.

BACKGROUND OF THE INVENTION

Prostate cancer is a form of cancer that develops in the prostrate, a gland in the male reproductive system. The cornerstone of treatment for men with prostate cancer (alternatively "PCa"), especially advance prostate cancer, has been androgen deprivation therapy ("ADT"), typically using a leutenizing hormone-releasing hormone (LH-RH) agonist. LH-RH is produced in the hypothalamus and induces release of luteinizing hormone (LH) from the pituitary [Schally, 2001]. As classically defined, luteininzing hormone then stimulates testosterone synthesis from Leydig cells in the male [Simoni, 1997]. ADT is typically achieved by chemical castration when luteinizing hormone-releasing hormone (LH-RH) production is suppressed at the level of the hypothalamus by LH-RH agonists.

Treatment with an LH-RH agonist can result in the palliation of painful bony metastases, decreases in the postvoid residual urine, and improved quality of life. Huggins and Hodges were awarded the Nobel Prize in 1967 for this pioneering work.

While ADT therapy is effective, the benefits are fleeting, lasting a median of 24 months. After that time, additional hormonal treatments may be attempted, but the benefit is even more transient and they are often ineffective. Unfortunately, men with castration resistant prostate cancer ("CRPC"), have few treatment options and unfortunately, often have symptomatic metastases. [Montgomery, 2008; Mostaghel, 2007].

Several studies have documented that androgen-dependent genes, like the prostate specific antigen (PSA) gene expression, are constitutively re-expressed in the absence of testicular androgens during CRPC progression [Gregory, 1998; Chen, 2004]. Progression of the castration-resistant phenotype is associated with androgen receptor amplification, mutation, responsiveness to promiscuous ligand interactions and activation of the AR signal transduction pathway through alterations in co-activators/co-repressors, and cross-talk with other signaling pathways [Feldman, 2001; Visakorpi, 1995]. However, CRPC still depends on and is enhanced by the presence of androgens.

Recently, several groups have shown that PCA cells are capable of producing testosterone directly from cholesterol [Montgomery, 2008; Dillard, 2008; Locke, 2008]. Up-regulation of genes and proteins encoding the necessary steroidogenic enzymes has been observed during CRPC progression [Locke, 2008], in metastases from patients with castration-resistant disease [Montgomery, 2008] and in an androgen-independent derivative of LNCaP cells [Dillard, 2008]. Although up-regulation of steroidogenic enzymes has been described in CRPC, the regulation of this androgen synthesis is poorly understood.

Clinical responses in patients with CRPC have been seen with the down-stream blockade of steroidogenesis in PCa cells by the CYP17 inhibitors ketoconazole and abiraterone. Ketoconazole, an antifungal with weak and non-specific CYP17 inhibitory properties, has been extensively used for the 'off-label' treatment of advanced CRPC. Efficacy data from phase II trials have shown that the response rate by prostate specific antigen (PSA) working group (PSAWG) criteria with ketoconazole range between 40-62% with a median duration of up to 7 months [Ang, 2009]. A trial of abiraterone acetate in chemotherapy-naïve men who had PCa that was resistant to multiple hormonal therapies demonstrated declines in PSA ≥30%, 50%, and 90% were observed in 14 (66%), 12 (57%), and 6 (29%) patients, respectively, and lasted between 69 to ≥578 days.

As such, there is a need for more effective control of androgen production in prostate cancer cells.

There is also a need for improved treatments for prostate cancer, including castration resistant prostate cancer.

There is also a need for new drug targets in prostate cancer, including prostate cancer cells.

The role and involvement of the Lueteninzing hormone/Luteinizing hormone receptor pathway in PCA progression is completely unexplored. The pituitary hormone LH was long thought to control steroidogenesis only in classical endocrine target cells (testicular Leydig cells) [Simoni, 1997].

SUMMARY OF THE INVENTION

One aspect of the present invention is the discovery that in the prostate, endocrine-, paracrine- and/or autocrine-produced luteinizing hormone drives prostate cancer cells towards castration resistance.

Another aspect of the present invention is the discovery that luteinizing hormone induces the steroidogenic machinery in prostrate cancer cells.

Another aspect of the present invention that luteinizing hormone increases prostate cancer cell viability in vitro.

Another aspect of the present invention is the discovery that androgen synthesis in prostate cancer cells is regulated by luteinizing hormone (LH). PCa cells also express mRNA and protein for luteinizing hormone receptor. Anther discovery of the present invention is that LH up-regulates genes of enzymes necessary for androgen synthesis which should result in an increased production of testosterone. Therefore, LH and LHR represent targets for anti-cancer treatment of PCa, but may also target other cancer where this pathway might be involved.

One embodiment of the present invention is a method of treating prostate cancer comprising disrupting the LH/LHR signaling pathway of prostate cancer cells. Preferably, the disruption of the LH/LHR pathway in the prostate cancer cells is accomplished by administering to a patient in need thereof an effective amount of an LH receptor inhibitor. Preferably, the LH receptor inhibitor is administered externally to the prostate cancer cells.

In accordance with the present invention, the LH receptor inhibitor binds, couples to or otherwise is operably linked to the LH Receptors on the prostate cancer cells that prevent LH from reacting with LH Receptor. Alternatively, the LH receptor inhibitor binds, couples to or otherwise is operably linked to the LH such that the LH cannot activate the LH Receptor. The LH receptor inhibitor is preferably an antibody or a small molecule.

Another embodiment of the present invention is a method of decreasing prostate cancer cell viability comprising disrupting the LH/LHR signaling pathway of a prostate cancer cell. Preferably, the disruption of the LH/LHR pathway in the prostate cancer cells is accomplished by administering to a patient in need thereof an effective amount of an LH receptor inhibitor. The LH receptor inhibitor is preferably administered externally to the prostate cancer cells.

The LH receptor inhibitor preferably binds, couples to or otherwise blocks the LH Receptors on the prostate cancer cells from reacting with LH. Alternatively, the LH receptor inhibitor binds, couples to or otherwise is operably linked to the LH such that the LH cannot activate the LH Receptor. Preferably, the LH receptor inhibitor is an antibody or a small molecule.

Another embodiment of the present invention is a method of down-regulating the expression of genes and enzymes required for steroidogenesis in prostate cancer cells comprising disrupting the LH/LHR signaling pathway of a prostate cancer cell. The disruption of the LH/LHR pathway in the prostate cancer cells is preferably accomplished by administering to a patient in need thereof an effective amount of an LH receptor inhibitor. Preferably, the LH receptor inhibitor is administered externally to the prostate cancer cells.

Preferably, the LH receptor inhibitor binds, couples to or otherwise blocks the LH Receptors on the prostate cancer cells from reacting with LH. Alternatively, the LH receptor inhibitor binds, couples to or otherwise is operably linked to the LH such that the LH cannot activate the LH Receptor. Preferably, the LH receptor inhibitor is an antibody or a small molecules.

Another embodiment of the present invention are pharmaceutical compositions for the treatment of prostate cancer comprising an LH receptor inhibitor.

Another embodiment of the present invention is a method of screening LH receptor inhibitors. The method preferably includes providing a first sample of prostate cancer cells, measuring the expression of one or more genes required for steroidogenesis in the prostate cancer cells, contacting a second sample of the prostate cancer cells with a potential LH modulator, and measuring the expression of the one or more genes required for steroidogenesis in second sample. The method also includes comparing the expression levels in the two samples. If the level of expression is lower in the second sample, the LH/LHR pathway is disrupted.

These and other embodiments of the present invention may be understood with reference to the entirety of the present disclosure, including without limiting the figures, the detailed description and the various examples described herein.

DETAILED DESCRIPTION OF THE INVENTION

Definitions

Figure 1A:
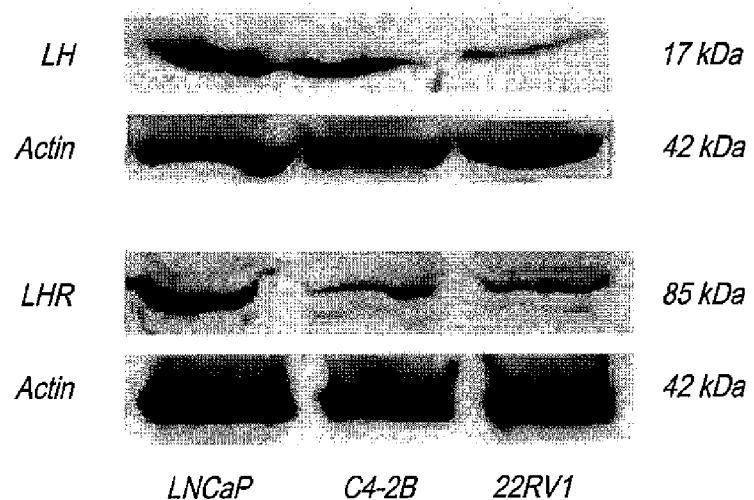
FIG. 1 is a chart showing the expression of luteinizing hormone (LH) and luteinizing hormone receptor (LHR) in PCA cells. Western blot analysis demonstrates LH and LHR expression in the human PCA cell lines LNCaP, 22RV1 and C4-2B, with the highest expression in LNCaP cells (A). Levels of mRNA expression for LHR as measured by real-time PCR (B). LH receptor expression (arrows) documented using IHC (C).

Unless otherwise indicated, all terms used herein have the meanings given below, and are generally consistent with same meaning that the terms have to those skilled in the art of the present invention. It is to be understood that this invention is not limited to the particular methodology, protocols, and reagents described, as these may vary.

All publications cited herein are expressly incorporated herein by reference for the purpose of describing and disclosing compositions and methodologies that might be used in connection with the invention.

As used herein, the term "prostate cancer" (PCA) refers to the art recognized use of the term which commonly appears in men. The term "prostate cancer" refers to both the appearance of a palpable tumor of the prostate, and also to microscopically detectable neoplastic or transformed cells in the prostate gland. In the latter case, the said cytologically-detectable prostate cancer may be asymptomatic, in that neither the patient nor the medical practitioner detects the presence of the cancer cells. Cancer cells are generally found in the prostates of men who live into their seventies or eighties, however not all of these men develop prostate cancer. In the event that prostate cancer metastasizes to additional sites distal to the prostate, the condition is described as metastatic cancer (MC), to distinguish this condition from organ-confined prostate cancer. PCA fatality results from metastatic dissemination of prostatic adenocarcinoma cells to distant sites, usually in the axial skeleton.

As used herein, the phrases "treating cancer," "treating prostate cancer", "treatment of cancer" and "treatment of prostate cancer" mean to inhibit the replication of cancer cells, inhibit the spread of cancer, decrease tumor size, lessen or reduce the number of cancerous cells in the body, or ameliorate or alleviate the symptoms of the disease caused by the cancer. The treatment is considered therapeutic if there is a decrease in mortality and/or morbidity, or a decrease in disease burden manifest by reduced numbers of malignant cells in the body.

The term "castration resistant prostate cancer" or "CRPC" refers to continuing growth or regrowth of cancer cells or tumors with serum testosterone controlled below a castrate level As used herein, the term "androgen regulated gene" or "androgen dependent gene" refers to a gene or portion of a gene whose expression is initiated or enhanced by an androgen (e.g., testosterone). The promoter region of an androgen regulated gene may contain an "androgen response element" that interacts with androgens or androgen signaling molecules (e.g., downstream signaling molecules).

The term "steroidogenesis" refers to the biological process by which steroids are generated from cholesterol and transformed into other steroids.

The term "LH" refers to luteinizing hormone.

The terms "luteinizing hormone receptors," "LH Receptors," or "LHRs" refers to any of the known leutenizing hormone receptors, which are generally transmembrane receptors that interact with leutenizing hormone (LH). LHRs are generally G protein-couple receptors.

As used herein, the term "luteinizing hormone receptor inhibitor" or "LH receptor inhibitor" refers to a species (e.g., but not limited to, an antibody and a small molecule) that disrupts the LH/LHR signaling pathway of prostate cancer cells. The term "LH receptor inhibitor" includes those species (e.g., but not limited to, antibodies and small molecules) that bind, couple to or are otherwise operably linked to the LH receptor in the prostate cancer cell and inhibits and exhausts the action of LH. The term "LH receptor inhibitor" also includes those species (e.g., but not limited to, antibodies and small molecules) that bind, couple or are otherwise operably linked to LH in a manner that prevents LH from binding to the LH receptor.

The term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "cAMP" refers to cyclic adenosine monophosphate (cAMP, cyclic AMP or 3'-5'-cyclic refers to adenosine monophosphate, which is a messenger important in many biological processes. cAMP is derived from adenosine triphosphate (ATP) and used for intracellular signal transduction.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antibody" refers to an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab').sub.2, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "small molecule" refers to compounds that are not macromolecules (see, e.g., Karp (2000) Bioinformatics Ontology 16:269-85; Verkman (2004) AJP-Cell Physiol. 286: 465-74). Thus, the term "small molecule" be considered those compounds that are, e.g., less than one thousand daltons (e.g., Voet and Voet, Biochemistry, $2^{nd}$ ed., ed. N. Rose, Wiley and Sons, New York, 14 (1995)). The phrase "small molecule" also encompasses small molecule gene products, e.g., DNAs, RNAs and peptides. Examples of natural small molecules include, but are not limited to, cholesterols, neurotransmitters, aptamers and siRNAs; synthesized small molecules include, but are not limited to, various chemicals listed in numerous commercially available small molecule databases, e.g., FCD (Fine Chemicals Database), SMID (Small Molecule Interaction Database), ChEBI (Chemical Entities of Biological Interest), and CSD (Cambridge Structural Database) (see, e.g., Alfarano et al. (2005) Nuc. Acids Res. Database Issue 33:D416-24).

Methods and Treatments Based on the Disruption of the LH/LH Receptor Signaling Pathway The luteinizing hormone receptor ("LH Receptor" or "LHR") belongs to the Gs-coupled seven-transmembrane domain receptor family, whose activation by luteinizing hormone (LH) leads to adenylyl cyclase stimulation. In testicular Leydig cells, the resulting accumulation of intracellular cAMP and the concomitant activation of cAMP-dependent PKA lead to the phosphorylation of numerous proteins, including StAR. One aspect of the present invention is the discovery that the same cAMP-dependent signaling pathway that regulates steroid synthesis in Leydig cells is involved in LH-induced steroidogenesis in prostate cancer cells.

The regulation of testicular steroidogenesis is dependent on the hypothalamo-pituitary-gonadal axis. The hypothalamic hormone, luteinizing hormone-releasing hormone (LH-RH), is produced in the hypothalamus and induces release of luteinizing hormone (LH) from the pituitary. As classically defined, LH stimulates testosterone synthesis from Leydig cells in the male. One aspect of the present invention is the observation that LH also up-regulates genes and enzymes necessary for steroid synthesis in prostate cancer cells. Furthermore, there is a significant increase in progesterone and testosterone production in LNCaP cells exposed to LH. Based on these observations and the fact that LH increases LNCaP cell viability to a similar degree as dihydrotestosterone (DHT), it appears that LH/LH Receptor signaling pathway is involved in the progression of PCA towards castration resistance.

Another aspect of the present is directed to methods, including treatment methods based upon disruption of the LH/LR Signaling pathway.

Another aspect of the present invention is directed to LH and the LH Receptor as new up-stream therapeutic targets in the steroid synthesis pathway of PCA cells.

The LH/LH Receptor signaling pathway may generally be defined as the cAMP-dependent signaling pathway that regulates LH-induced steroidogenesis. One critical part of the LH/LH Receptor signaling pathway is the activation of the LH Receptor by LH. One aspect of the present invention is directed to methods based upon disrupting the LH/LH receptor signaling pathway by preventing the activation of the LH Receptor by LH.

One embodiment of the present invention is a method of treating prostate cancer comprising disrupting the LH/LH receptor signaling pathway of prostate cancer cells. Another embodiment of the present invention is a method of decreasing prostate cancer cell viability comprising disrupting the LH/LHR signaling pathway of a prostate cancer cell. Still another embodiment of the present invention is a method of down-regulating the expression of genes and enzymes required for steroidogenesis in prostrate cancer cells comprising disrupting the LH/LHR signaling pathway of a prostate cancer cell.

Preferably, in each of these methods, the disruption of the LH/LH Receptor signaling pathway is complete, i.e., resulting in the complete elimination of the LH/LH receptor signaling pathway. However, it is not necessary that the disruption be complete. Generally, it is required that the LH/LH signaling pathway result in significantly less activation of the pathway than in untreated cells and the lessened activation results in successfully achieving the result intended by the method. It should be emphasized that "treating cancer" is intended to broadly mean to inhibit the replication of cancer cells, decrease the viability of cancer cells, inhibit the spread of cancer, decrease tumor size, lessen or reduce the number of cancerous cells in the body, or ameliorate or alleviate the symptoms of the disease caused by the cancer. Preferably, but not necessarily, the treatment of cancer is considered therapeutic if there is a decrease in mortality and/or morbidity, or a decrease in disease burden manifest by reduced numbers of malignant cells in the body or a decreased viability of the cancer cells.

Preferably, the disruption of the LH/LHR pathway in the prostate cancer cells is accomplished by administering to a patient in need thereof an effective amount of an LH receptor inhibitor. An effective amount of the LH Receptor Inhibitor may generally be determined by methods known to those of ordinary skill in the art, including those described in the examples. Preferably, the LH receptor inhibitor is administered externally to the prostate cancer cells.

Preferably, the LH/LH receptor disrupts the LH/LH receptor signaling pathway by preventing activation of the LH receptor by LH. Thus, in on aspect the present invention, the LH receptor inhibitor binds, couples to or otherwise is operably linked to the LH Receptors on the prostate cancer cells in a manner that prevent LH from activating the LH Receptor. Alternatively, the LH receptor inhibitor binds, couples to or otherwise is operably linked to the LH such that the LH cannot activate the LH Receptor.

The LH receptor inhibitor is preferably an antibody or a small molecule mad according to the methods described herein. The LH receptor inhibitor is preferably incorporated in to a pharmaceutical compositions as described herein.

Antibodies Disrupting the LH/LH Receptor Signaling Pathway

The present invention includes LH Receptor Inhibitors that are isolated antibodies that disrupt the LH/LH Receptor signaling pathway. The antibodies include antibodies that bind, couple to or otherwise are operably linked to the LH Receptors on the prostate cancer cells such that LH is prevented from activating the LH Receptor. Alternatively, the antibodies may bind, couple to or otherwise be operably linked to the LH such that the LH cannot activate the LH Receptor.

The antibody, or antibody fragment, can be any monoclonal or polyclonal antibody, or fragment thereof, that specifically recognizes the LH or the LH Receptor and disrupts the LH/LH Receptor Signaling pathway. In some embodiments, the monoclonal antibodies, or fragments thereof, are chimeric or humanized antibodies that specifically bind to LH or the LH Receptor of the cancer cells. In one embodiment of the present invention, the antibodies and pharmaceutical compositions comprising the antibodies are used to treat cancer in a human patient by administering an effective amount of an antibody against LH or the LH Receptor.

Polyclonal antibodies can be prepared by any known method. Polyclonal antibodies can be raised by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will, specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody disrupting the LH/LH Receptor signaling pathway is a humanized antibody. Humanized antibodies are antibodies that contain minimal sequences from non-human (e.g. murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239: 1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545, 806; 5,569,825; 5,625,126; 5,633,425; and 5,661,016.

In certain embodiments of the invention, it may be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from *E. coli* or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

It may further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

Small Molecules Disrupting the LH/LH Receptor Signaling Pathway

Disrupting the LH/LH Receptor signaling pathway in a cancer cell (or patient) may also be achieved through the use of small molecules (usually organic small molecules or peptides) that inhibit or block the activation of the LH Receptors on cancer cells. The small molecules include small molecules that bind, couple to or otherwise are operably linked to the LH Receptors on the cancer cells such that LH is prevented from activating the LH Receptor. Alternatively, the small molecule binds, couples to or otherwise is operably linked to the LH such that the LH cannot activate the LH Receptor. Novel small molecule LH receptor inhibitors may be identified by the screening methods described herein, formulated into pharmaceutical composition and may be used in the treatment methods of the present invention as also described herein.

Candidate small molecule LH Receptor Inhibitors of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb at al., Proc. Nat. Acad. Sci. USA 91:11422 [1994]; Zuckermann at al., J. Med. Chem. 37:2678 [1994]; Cho at al., Science 261:1303 [1993]; Carrell at al., Angew. Chem. Int. Ed. Engl. 33.2059 [1994]; Carell at al., Angew. Chem. Int. Ed. Engl. 33:2061 [1994]; and Gallop et al., J. Med. Chem. 37:1233 [1994].

Libraries of compounds can be presented in solution (e.g., Houghten, Biotechniques 13:412-421 [1992]), or on beads (Lam, Nature 354:82-84 [1991], chips (Fodor, Nature 364: 555-556 [1993]), bacteria or spores (U.S. Pat. No. 5,223,409; herein incorporated by reference), plasmids (Cull at al., Proc. Nat. Acad. Sci. USA 89:18651869 [1992]) or on phage (Scott and Smith, Science 249:386-390 [1990]; Devlin Science 249: 404-406 [1990]; Cwirla at al., Proc. Natl. Acad. Sci. 87:6378-6382 [1990]; Felici, J. Mol. Biol. 222:301 [1991]).

The candidate small molecule LH Receptor inhibitors can then screened according to the screening methods of the present invention to arrive at appropriate LH Receptor inhibitors for formulating into pharmaceutical compositions and for use in connection with the methods of the present invention.

LH Receptor Inhibitor Screening Methods

Figure 2A:
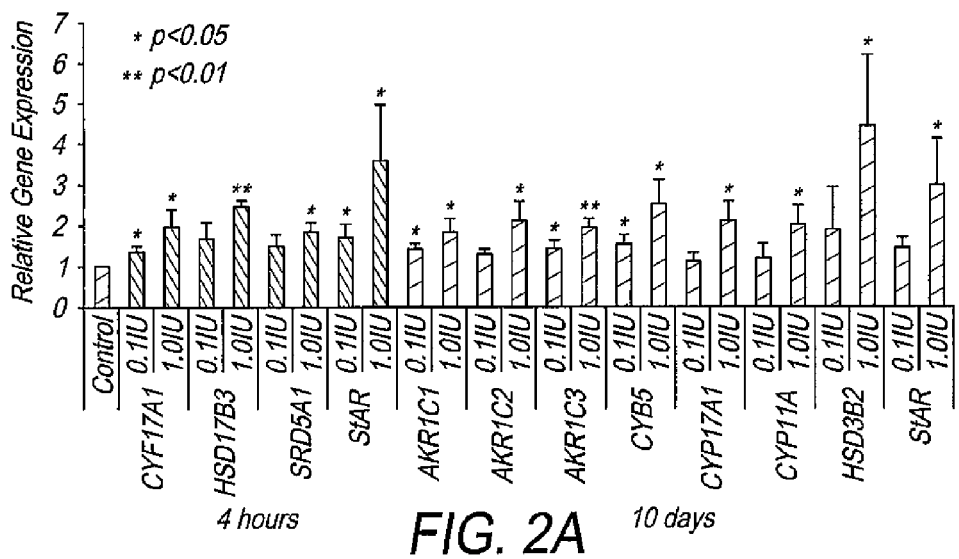
FIG. 2 is a graph showing the steroidogenic gene expression after exposure to luteinizing hormone (LH). Real-time PCR analysis of steroidogenic gene expression following exposure to LH for 4 hours (red) and 10 days (purple). A dose- and time-dependent increase in steroidogenic gene expression was noted in LNCaP (A), 22RV1 (B), and C4-2B (C) PCA cells.

In some embodiments, the present invention provides drug screening assays (e.g., to screen for anticancer drugs). The screening methods of the present invention utilize the expression of steroidogenic genes and enzymes involved in androgen synthesis from cholesterol as a marker for disruption of the LH/LH Receptor pathway in cancer cells. The present invention documents mRNA expression for the enzymes involved in androgen synthesis from cholesterol (AKR1C1, AKR1C2, AKR1C3, CYB5, CYP11A1, CYP17A1, FASN, HSD3B2, HSD17B2, HSD17B3, RDH5, SRD5A1, SRD5A2, StAR) (FIG. 2). Specifically, exposure of LNCaP cells to LH for 4 hours in doses of 0.1 and 1.0 IU/ml resulted in a dose-dependent increase in the expression of StAR, HSD17B3, SRD5A1 and CYP17A1 that met statistical significance when compared to controls (FIG. 2A). Thus, a decrease in the amount of LH led to a dose dependent decrease in expression.

In some embodiments, the present invention provides methods of screening for compound that alter (e.g., increase or decrease) the expression of genes and enzymes involved the synthesis of androgen from cholesterol, including StAR, HSD17B3, SRD5A1 and CYP17A1. In some embodiments, candidate compounds are small molecules that bind to LH or LHR. In other embodiments, candidate compounds are antibodies that specifically bind to LH or LHR.

In one screening method, candidate compounds are evaluated for their ability to alter stem steroidogenic gene or enzyme expression by contacting a cell having an LH Receptor with a compound, and then with LH and assaying for the effect of the candidate compounds on expression levels of steroidogenic genes and/or enzymes. In some embodiments, the effect of candidate compounds on expression of a cancer marker gene is assayed by detecting the level of steroidogenic genes and/or enzymes expressed by cancer cells. The expression can be detected by any suitable method, including the methods of the examples described herein.

Pharmaceutical Compositions

The present invention further provides pharmaceutical compositions comprising the LH Receptor Inhibitors of the present invention. The pharmaceutical compositions of the present invention can be administered in a number of ways depending upon whether local or systemic treatment is desired and upon the area to be treated. Administration is typically oral or parenteral. Parenteral administration includes intravenous, intraarterial, subcutaneous, intraperitoneal or intramuscular injection or infusion; or intracranial, e.g., intrathecal or intraventricular, administration.

Compositions and formulations for oral administration include powders or granules, suspensions or solutions in water or non-aqueous media, capsules, sachets or tablets. Thickeners, flavoring agents, diluents, emulsifiers, dispersing aids or binders can be desirable.

Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into dosage forms such as, but not limited to tablets, capsules and sterile solutions. The compositions of the present invention may also be formulated as suspensions in aqueous, non-aqueous or mixed media. Aqueous suspensions can further contain substances that increase the viscosity of the suspension including, for example, sodium carboxymethylcellulose, sorbitol and/or dextran. The suspension can also contain stabilizers.

Where appropriate, agents that enhance uptake of oligonucleotides at the cellular level can also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The LH Receptor Inhibitors of the present invention can additionally contain other adjunct components conventionally found in pharmaceutical compositions. Thus, for example, the compositions can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Combination formulations of LH Receptor inhibitors with other chemotherapeutic agents are also within the scope of this invention. Two or more combined compounds can be used together or sequentially.

Dosing is generally done in an amount necessary to administer to the patient an effective amount the LH Receptor Inhibitor as described herein. Dosing is also dependent on severity and responsiveness of the disease state to be treated, with the course of treatment typically several months, or until a cure is effected or a diminution of the disease state is achieved (e.g. reduction in tumor size). Optimal dosing schedules can be calculated from measurements of drug accumulation in the body of the patient. The administering physician can determine optimum dosages, dosing methodologies and repetition rates.

EXAMPLES

The following examples are provided in order to demonstrate and further illustrate certain embodiments and aspects of the present invention and are not to be construed as limiting the scope thereof. Other procedures known to those skilled in the art may alternatively be utilized. Indeed, those of ordinary skill in the art can readily envision and produce further embodiments, based on the teachings herein, without undue experimentation.

Materials and Methods

Cells and reagents. The PCA cell lines LNCaP and 22Rv1 were obtained from American Type Culture Collection (ATCC, Rockville, Md.) and the C4-2B cell line from the laboratory of Dr. Coetzee (University of Southern California, Los Angeles Calif.) and maintained in RPMI 1640 medium containing 10% FBS (Gibco, Grand Island, N.Y.) at 5% CO2 and 37° C. Human LH was obtained from Fitzgerald Industries Intl. (Concord, Mass.). All PCR primers were purchased from Invitrogen (Carlsbad, Calif.).

Real-time PCR analysis. The quantitative measurement of target mRNA was performed using a real-time PCR system (Applied Biosystems 7500, Foster, Calif.) according to the manufacturer's instructions. PCR amplifications were performed with the SYBR Green PCR core reagent (Applied Biosystems) in a volume of 10 µl, with 1 µl of the reverse transcription products. LH and steroidogenic enzyme RNA quantification were assayed with the following primers: AKR1C1, 5'-attcccatcgaccagagttg-3' (forward), 5'-tttgggat-cacttcctcacc-3' (reverse); AKR1C2, 5'-gatcccatcgagaa-gaacca-3' (forward), 5'-acacctgcacgttctgtctg-3' (reverse); AKR1C3, 5'-atttggcacctatgcacctc-3' (forward), 5'-cacactgc-catctgcaatct-3' (reverse); CYB5, 5'-gaagagcctgattggacac-3' (forward), 5% aaatttgagcgcagaaagga-3' (reverse); CYP11A1, 5'-gcaacgtggagtcggtttat-3' (forward), 5'-aggggcaaaaagttct-tggt-3' (reverse); CYP17A1, 5'-gagttcgagaccagcctgac-3' (forward), 5'-gcttctcgggttcaagtgag-3' (reverse); FASN, 5'-cccac-ctacgtactggccta-3' (forward), 5'-cttggccttgggtgtgtact-3'  (reverse); HSD3B2, 5'-tggactcctctgtccagctt-3' (forward), 5'-ctagcgtgacccagaagagg-3' (reverse); HSD17B2, 5'-ggcaactcaagctcaaggac-3' (forward), 5'-actcagcgtggcttct-tcat-3' (reverse); HSD17B3, 5'-ttttgctgctgttgttcctg-3' (forward), 5'-gatcgcactactgcactcca-3' (reverse); RDH5, 5'-cag-caatgcctttgtettca-3' (forward), 5'-taccagccacaccagcatta-3' (reverse); SRD5A1, 5'-tcgcatgaaaacttgcgtag-3' (forward), 5'-ttgaagttccacagccactg-3' (reverse); SRD5A2, 5'-gccctctcct-catagtgetg-3' (forward), 5'-ccaggttcatgccttttgt-3' (reverse); StAR, 5'-ggctactcagctcgacctc-3' (forward), 5'-catcccactgt-caccagatg-3' (reverse); and LHR, 5'-tcaattcttgtccaatcca-3' (forward), 5'-ccatttttgcagttggaggt-3' (reverse). Each gene under each condition was amplified in triplicate. Analysis was performed with Applied Biosystems' software and the relative expression was standardized using expression of 18S as a reference, 5'-ggagagggagcctgagaaac-3' (forward), 5'-tcgg-gagtgggtaatttge-3' (reverse). Results were plotted as the mean ±SD from three experiments.

Western blot analysis. Equal amounts of protein (10 µg) from cell lysates were heated at 95° C. for 5 min in the sample loading buffer, then subjected to SDS-PAGE and transferred to nitrocellulose membranes. The blots were probed overnight at 4° C. with the appropriate commercially available primary antibodies, including anti-LHR rabbit polyclonal antibody (1:200, Santa Cruz Biotech), anti-LH mouse monoclonal antibody (1:1000, Santa Cruz Biotech, Santa Cruz, Calif.), anti-CYP-17A1 rabbit polyclonal (1:400, Abeam, Cambridge, Mass.), anti-CYP-11A1 rabbit polyclonal antibody (1:400, Abeam), and anti-StAR mouse monoclonal antibody (1:500, Abeam). After incubation with the corresponding horseradish peroxidase-conjugated secondary antibodies, the blots were further probed with corresponding HRP-conjugated antibodies and visualized by enhanced chemiluminescence (Pierce, Rockford, Ill.). Rabbit anti-β-actin antibody (1:2,000, Sigma Chemical Co.) served as loading control. Quantification of the bands was performed with Quantity One software (Bio-Rad Lab, Hercules, Calif.).

Cyclic AMP assay. The cAMP assay was performed using the correlate-EIA direct cAMP enzyme immunoassay kit (Assay Designs, Inc., Ann Arbor, Mich.) according to manufacturer's instructions. The cAMP levels were noted in cells treated with LH and in negative controls.

Protein kinase A assay. PKA activity was measured using a PKA kinase activity assay kit (Assay Designs, Inc., Ann Arbor, Mich.) according to manufacturer's instructions. The PKA activity was measured in cells treated with LH and in negative controls. Each sample was standardized by protein concentration.

Immunohistochemistry. Deparaffinization of PCA tissue was performed with xylene and tissue was rehydrated in graded ethanol solutions and rinsed in tap water. The slides were buffered with dilute hydrogen peroxide and blocked with 20% fetal bovine serum, then incubated overnight at 4° C. with rabbit polyclonal against LHR (Santa Cruz Biotech). The tissue was then incubated for 1 hour at room temperature with the secondary antibody (1:1000 dilution of conjugated rabbit anti-mouse antibody; Dako, Carpinteria, Calif.). The slides were developed with diaminobenzidine tetrahydrochloride solution (Dako), lightly counterstained with hematoxylin and cover slipped.

Steroid analysis by radioimmunoassay. Concentrations of the steroids progesterone and testosterone were determined using radioimmunoassay as described previously (11-13). Data were normalized per $10^6$ cells and expressed as the mean ±SD from three 100 ml cell culture dishes per group.

Cell viability assay. Cells were treated with LH at varying concentrations and incubated with 20 µl of Celltiter 96®

Aq$_{ueous}$ One Solution Cell Proliferation assay (Promega Co., Madison, Wis.) according to the manufacturer's instruction. The optical density was determined using a microplate reader (SpectraMax Plus) at 490 nm. The cell viability following LH treatment was expressed vs. negative control and plotted as the mean ±SD.

Statistics. Results were reported as means ±SD of at least three experiments. Student t-test was used for statistical analysis and the differences between two means with a p value <0.05 were considered significant.

Example 1

PCA Cells Express LH and LHR

Figure 1B:
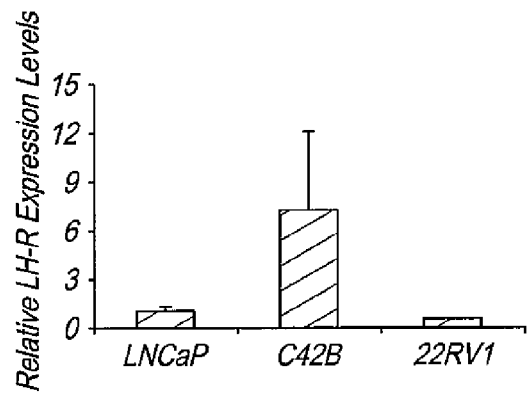
Figure 1C:
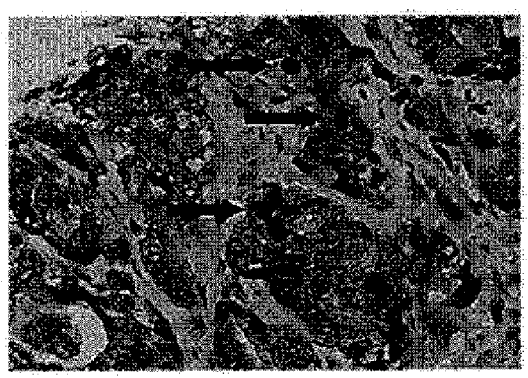

Western blot analysis demonstrates LH and LHR protein expression in the human PCA cell lines LNCaP, 22RV1 and C4-2B. The highest expression for both LH and LHR was seen in the androgen-sensitive LNCaP cell line (FIG. 1A). LHR gene transcription was noted in all three cell lines as measured by real-time PCR (FIG. 1B). LHR expression in human prostate cancer tissue was also detected with IHC (FIG. 1C).

Example 2

Figure 2B:
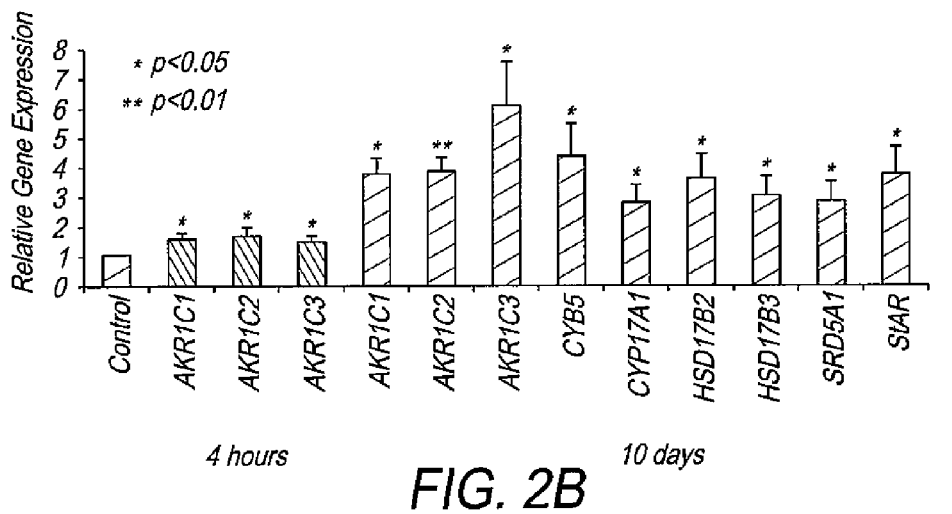
Figure 2C:
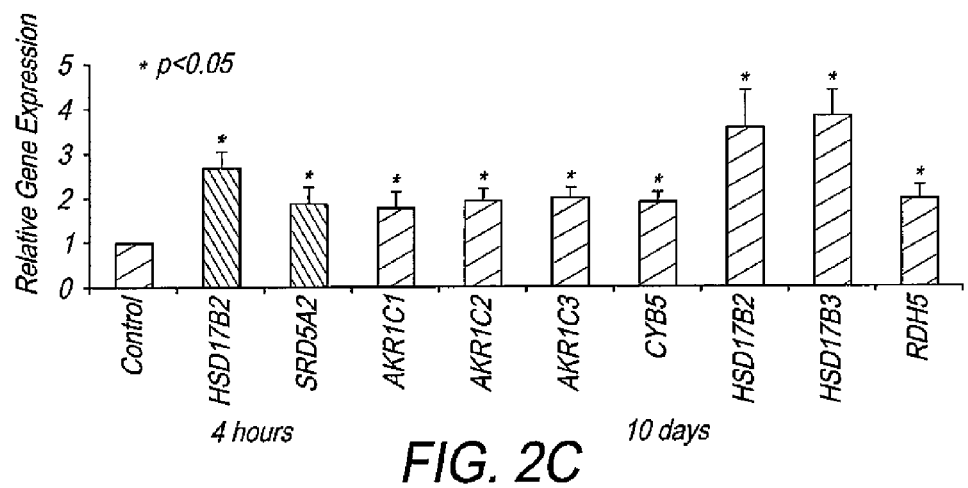
Figure 3A:
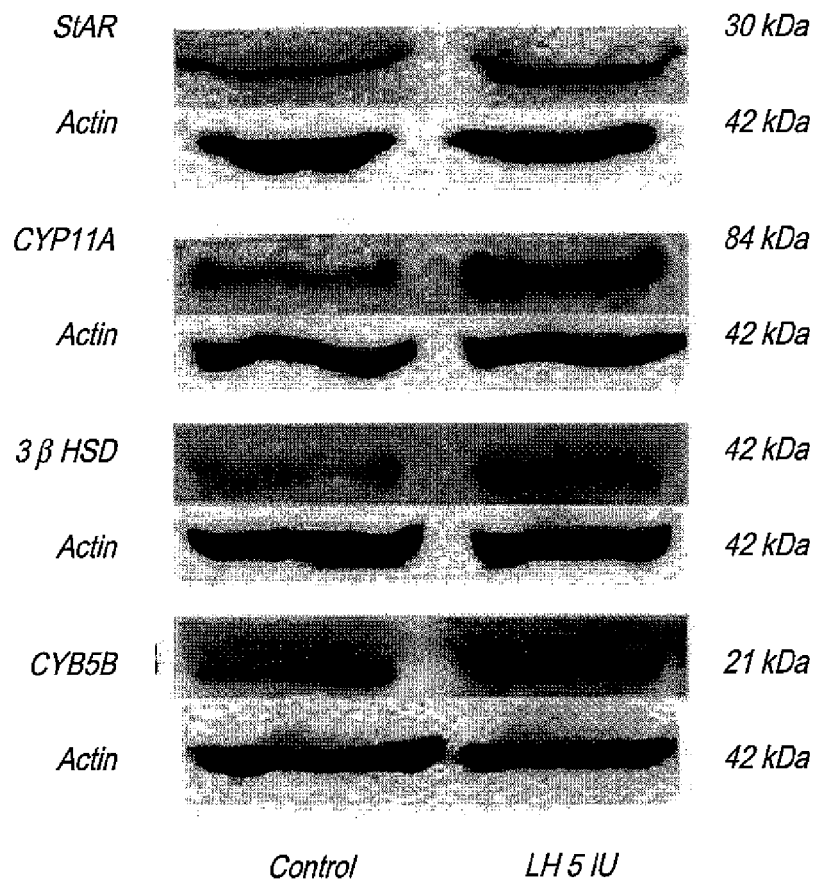
FIG. 3 shows changes in the steroidogenic machinery of PCA cells exposed to luteinizing hormone (LH). Western blot results show increased expression of key steroidogenic enzymes in LNCaP cells treated with LH (5.0 IU/ml) for 96 hours (A). Densitometric measurement revealed an approximately two-fold increase in the expression of proteins in LH treated cells. Progesterone and testosterone levels in LNCaP cells treated with LH (1.0 IU/ml) for 10 days were measured by RIA (B). LH treatment significantly increased progesterone and testosterone synthesis in LNCaP cells as compared to untreated controls.
Figure 3B:
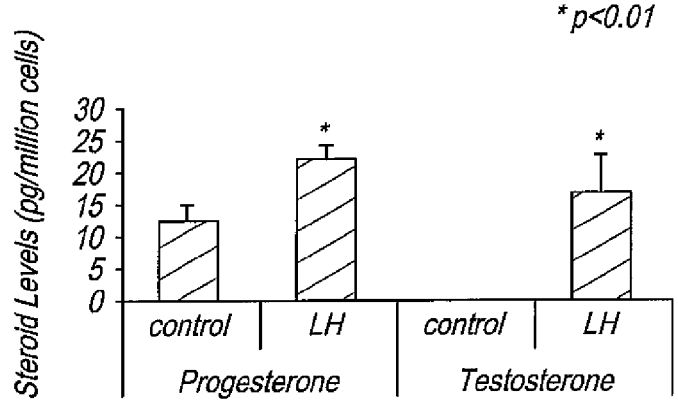

Addition of External LH Increases Expression of Steroidogenic Genes and Enzymes as Well as Steroids in PCA Using real-time PCR analysis in LNCaP, C4-2B and 22Rv1 cells, we have documented mRNA expression for the enzymes involved in androgen synthesis from cholesterol (AKR1C1, AKR1C2, AKR1C3, CYB5, CYP11A1, CYP17A1, FASN, HSD3B2, HSD17B2, HSD17B3, RDH5, SRD5A1, SRD5A2, StAR) (FIG. 2). Exposure of LNCaP cells to LH for 4 hours in doses of 0.1 and 1.0 IU/ml resulted in a dose-dependent increase in the expression of StAR, HSD17B3, SRD5A1 and CYP17A1 that met statistical significance when compared to controls (FIG. 2A). Ten day exposure to LH resulted in up-regulation of twice as many genes involved in androgen synthesis (FIG. 2A). At the dose of 1.0 IU/ml of LH, most of the genes examined displayed an approximately 2-4 fold increase in expression as compared to controls (FIG. 2A). Ten day treatment of C4-2B and 22Rv1 cells with LH at a concentration of 1.0 IU/ml tripled the number of significantly up-regulated genes as compared to short-term exposure. There was a 2-6 fold increase in the expression levels of those genes in both cell lines as compared to controls (FIG. 2B, FIG. 2C). Exposure of LNCaP cells for 96 hours to LH (5.0 IU/ml) resulted in increased expression of the steroidogenic proteins StAR, CYB5B, CYP11A and 3βHSD as compared to untreated controls (FIG. 3A). LH treatment of LNCaP cells at a concentration of 1.0 IU/ml for 10 days significantly stimulated the production of progesterone and testosterone compared to controls as measured by RIA (FIG. 3B).

These results also demonstrate that lower external LH results in a dose-dependent decrease in the expression of StAR, HSD17B3, SRD5A1 and CYP17A1. Without being limited to any theory, it is believed that this decrease is due to less (or fewer) interactions between the LH and LH Receptor, thus resulting in lesser activation of the LH/LH Receptor pathway.

Example 3

LH Activates cAMP/PKA Signaling in PCA Cells

Figure 4A:
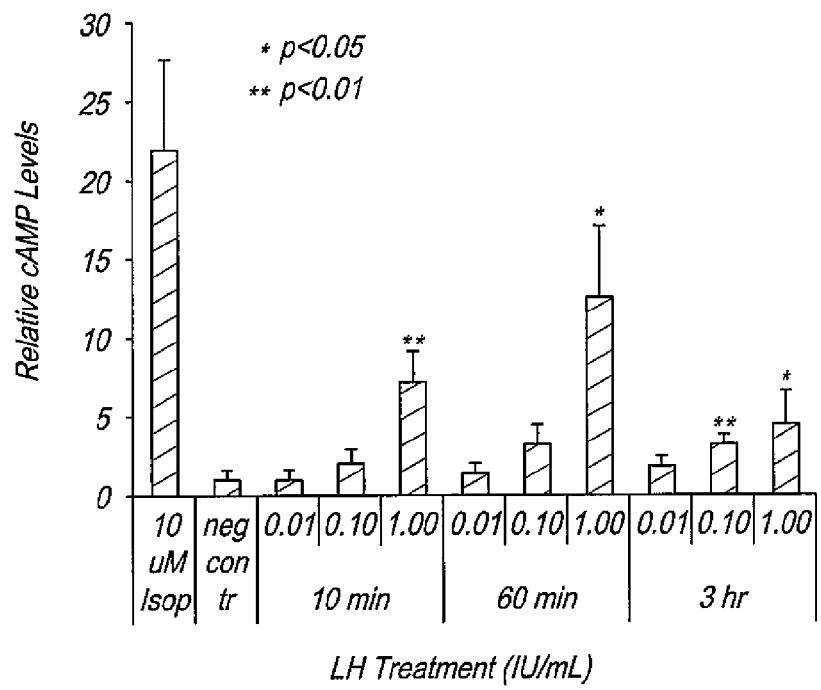
FIG. 4 shows the effect of luteinzing hormone (LH) on cAMP levels and PKA activation in LNCaP cells. LH (1.0 IU/ml) induced a transient increase in cAMP level (2.8-fold, $p<0.05$) in LNCaP cells (A). LH treatment also led to an increase in PKA activity (34.1%, $p<0.05$) as compared to negative controls (B).
Figure 4B:
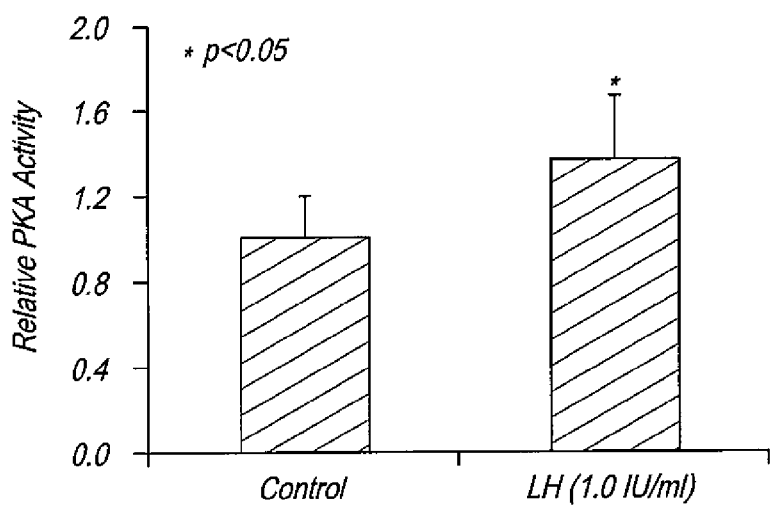

LH increased cAMP levels (2.8 fold, p<0.05) in LNCaP cells in a dose- and time-dependent manner (FIG. 4A). Treatment with LH also induced an increase in PKA activity (34.1%, p<0.05) compared to negative controls (FIG. 4B).

Example 4

LH enhances Cell Viability in PCA Cells

Figure 5:
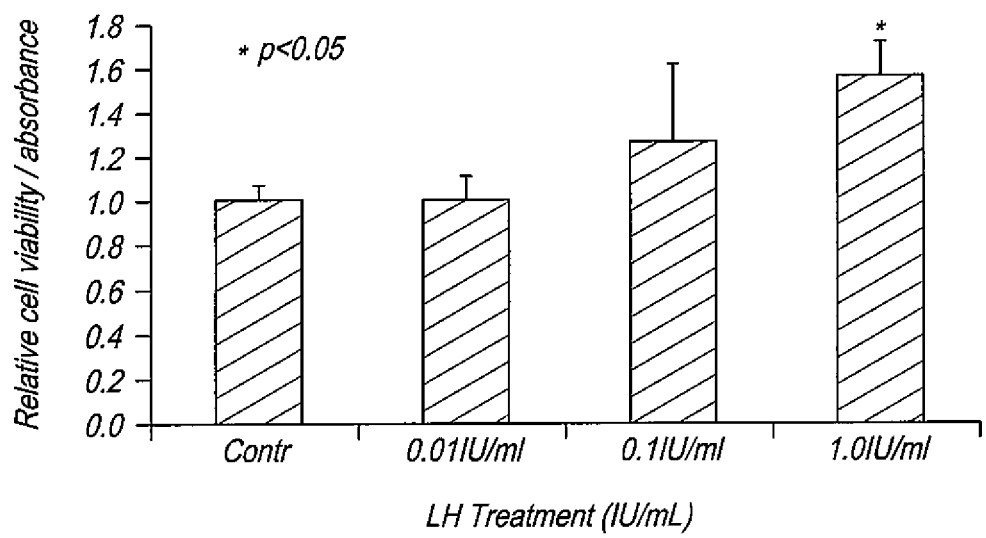
FIG. 5 shows the viability of LNCaP cells treated with LH for 72 hours. LH treatment (1.0 IU/ml) of LNCaP cells induced a 37% increase in cell viability compared to the control group ($p<0.05$).

External LH treatment of LNCaP cells induced a dose-dependent increase in cell viability. At the highest concentration of LH (1.0 IU/ml), there was a 37% increase in cell viability compared to the control group (p<0.05) (FIG. 5).

These results also demonstrate that lower external LH decreases results in a dose dependent decrease in cell viability. Without being limited to any theory, it is believed that this is because of less (or fewer) interactions between the LH and the LH Receptors, thus resulting in lesser activation of the LH/LHR pathway.

Example 5

Figure 6:
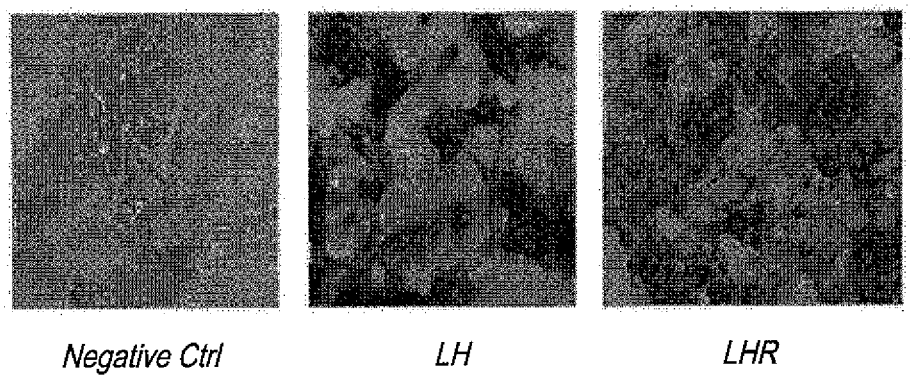
FIG. 6 shows the IHC staining for LH and LHR, in human PCa cell lines LNCaP and PC-3.
Figure 6:
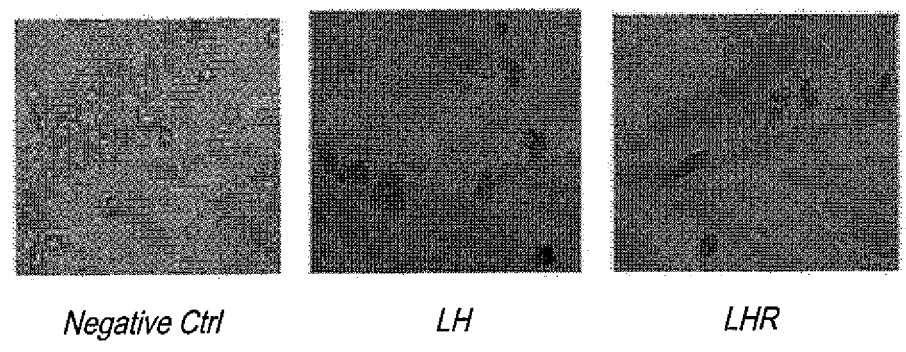

LH and LHR, Luteinizing Hormone-Releasing Hormone (LH-RH) are Expressed in Human PCa Cell Lines PCa cells were cultured in RPMI 1640 medium containing 10% FBS before being formalin-fixed and stained with LH and LHR, antibodies. FIG. 6 shows LH and LHR expression in human PCa cell lines LNCaP and PC-3 as measured by immunohistochemistry (IHC). LH and LHR were significantly more expressed in androgen-sensitive and AR positive LNCaP cells as compared to the androgen-independent and AR negative cell line PC-3.

Example 6

LH Induces Gene Expression of Steroidogenic Enzymes in PCa Cells

Figure 7:
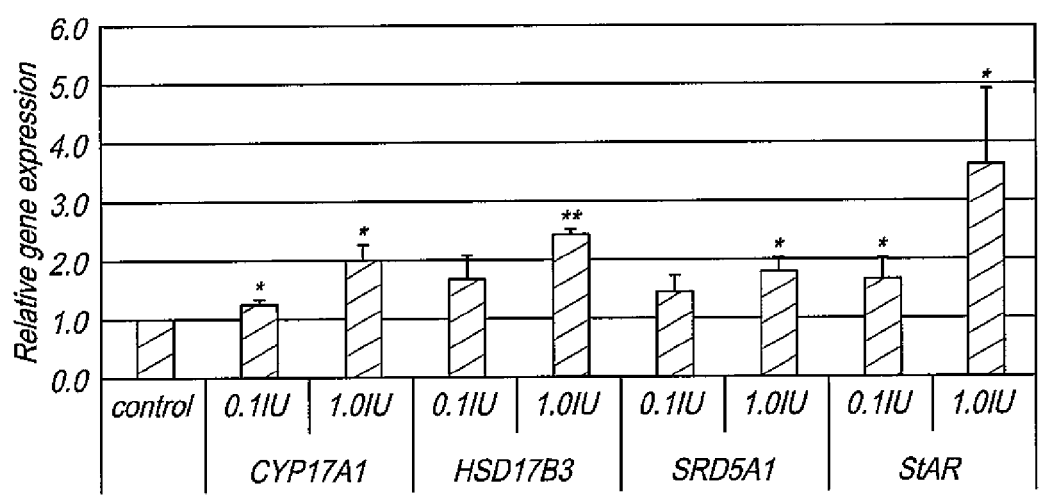
FIG. 7 shows the relative gene expression of steroidogenic enzymes in LNCaP cells following 4 hours exposure to LH.

LNCaP cells treated with LH at doses of 0.1 and 1.0 IU/ml for four hours. $5 \times 10^5$ cells were seeded and treated with LH for four hours on a 100-mm plastic dish in serum-free RPMI-1640 medium. The quantitative measurement of target mRNA was performed using a real time PCR system (Applied Biosystems 7500, Foster, Calif.) according to the manufacturer's instructions, with 50 cycles for the melting (95° C., 15 s) and annealing/extension (59° C., 60 s) steps. PCR amplifications were performed with SYBR Green PCR core reagent (Applied Biosystems) in a total volume of 10 µl, with 1 µl of the reverse transcription products. Each gene in each experimental condition was amplified in triplicate. Relative gene expression levels (y axis) for the indicated enzymes were normalized by expression of the 18S and compared to the control in the same sample. Unpaired two-sample t-tests were used and a p value <0.05 was considered significant. Results were plotted as mean ±S.D. from at least three experiments. LH treatment for 4 hours significantly (p<0.05) and dose-dependently stimulated the expression of 4 genes (out of 14 we tested) involved in steroidogenesis in PCa cells. FIG. 7 shows changes in gene expression levels of the steroidogenic enzymes.

Figure 8:
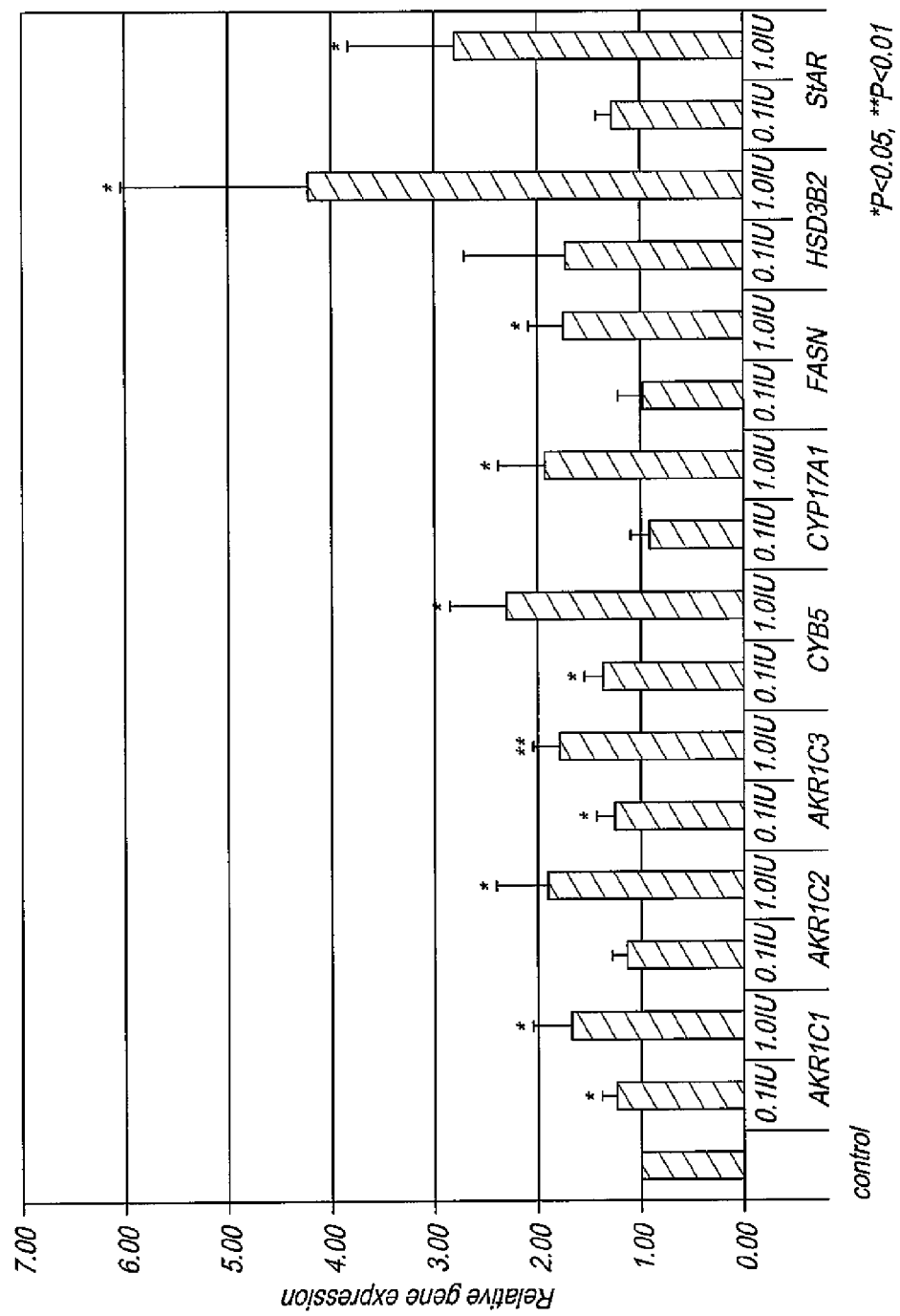
FIG. 8 shows the Relative gene expression of steroidogenic enzymes in LNCaP cells following 10 days exposure to LH.
Figure 9:
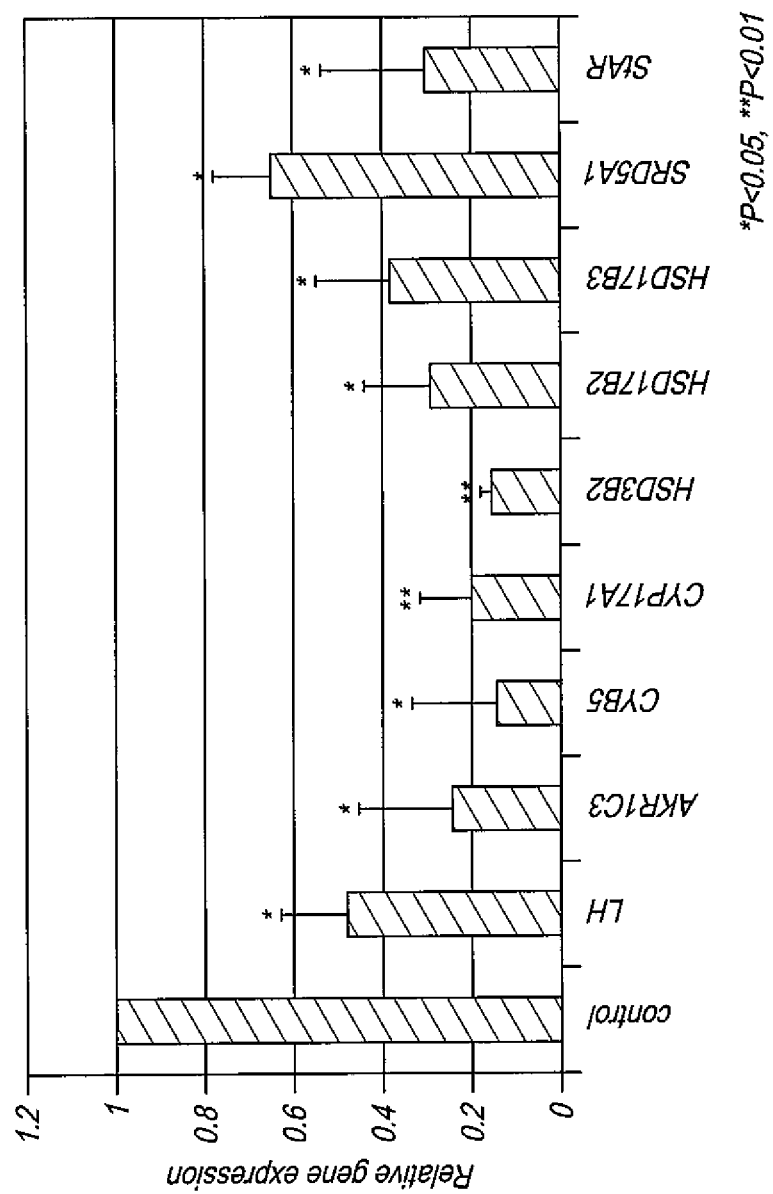
FIG. 9 shows the relative gene expressions of LH-beta and steroidogenic enzymes in LNCaP cells following 4 hours exposure to an LH-RH analog.

LNCaP cells (5×10$^5$) were seeded and treated with LH at doses of 0.1 and 1.0 IU/ml for 10 days on a 100-mm plastic dish in RPMI-1640 medium supplemented with 1% charcoal-stripped FBS. LH and medium were replaced every two days. The quantitative measurement of target mRNA was performed using a real time PCR system (Applied Biosystems 7500, Foster, Calif.) according to the manufacturer's instructions, with 50 cycles for the melting (95° C., 15 s) and annealing/extension (59° C., 60 s) steps. PCR amplifications were performed with SYBR Green PCR core reagent (Applied Biosystems) in a total volume of 10 µl, with 1 µl of the reverse transcription products. Each gene at each experimental condition was amplified in triplicate. Relative gene expression levels (y axis) for the indicated enzymes were normalized by expression of the 18S and compared to the control in the same sample. Unpaired two-sample t-tests were used and a p value <0.05 was considered significant. Results were plotted as mean ±S.D. from at least three experiments. Long-term treatment with LH for 10 days doubled the number of activated genes for steroidogenic enzymes (from 4 to 8) as compared to short-term 4-hour exposure to LH. FIG. 8 shows changes in gene expression levels of steroidogenic enzymes in the LNCaP cells. The 8 genes involved in steroidogenesis in PCa cells were significantly (P<0.05) and dose-dependently stimulated following 10-day treatment with LH.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It should be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It should be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein, including but not limited to patents, patent applications, and non-patent literature, are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize, or be able to ascertain using no more than routine experimentation, many equivalents to the specific embodiments of the method and compositions described herein. Such equivalents are intended to be encompassed by the following claims.

References

1. Dillard P R, Lin M F, Khan S A: Androgen-independent prostate cancer cells acquire the complete steroidogenic potential of synthesizing testosterone from cholesterol. Mal Cell Endocrinol 295(1-2):115, 2008.

2. Locke J A, Guns E S, Lubik A A, Adomat H H, Hendy S C, Wood C A, Ettinger S L, Gleave M E, Nelson C C: Androgen levels increase by intratumoral de novo steroidogenesis during progression of castration-resistant prostate cancer. Cancer Res 68(15):6407, 2008.

3. Montgomery R B, Mostaghel E A, Vessella R, Hess D L, Kalhorn T F, Higano C S, True L D, Nelson P S: Maintenance of intratumoral androgens in metastatic prostate cancer: a mechanism for castration-resistant tumor growth. Cancer Res 68(11):4447, 2008.

4. Mostaghel E A, Page S T, Lin D W, Fazli L, Coleman I M, True L D, Knudsen B, Hess D L, Nelson C C, Matsumoto A M, Bremner W J, Gleave M E, Nelson P S: Intraprostatic androgens and androgen-regulated gene expression persist after testosterone suppression: therapeutic implications for castration-resistant prostate cancer. Cancer Res 67(10):5033, 2007.

5. Gregory C W, Hamil K G, Kim D, Hall S H, Pretlow T G, Mohler J L, French F S: Androgen receptor expression in androgen-independent prostate cancer is associated with increased expression of androgen-regulated genes. Cancer Res 58(24):5718, 1998.

6. Chen C D, Welsbie D S, Tran C, Baek S H, Chen R, Vessella R, Rosenfeld M G, Sawyers C L: Molecular determinants of resistance to antiandrogen therapy. Nat Med 10(1):33, 2004.

7. Feldman B J, Feldman D: The development of androgen-independent prostate cancer. Nat Rev Cancer 1(1):34, 2001.

8. Visakorpi T, Hyytinen E, Koivisto P, Tanner M, Keinanen R, Palmberg C, Palotie A, Tammela T, Isola J, Kallioniemi O P: In vivo amplification of the androgen receptor gene and progression of human prostate cancer. Nat Genet 9(4):401, 1995.

9. Geller J, Albert J, Nachtsheim D, Loza D, Lippman S: Steroid levels in cancer of the prostate—markers of tumor differentiation and adequacy of anti-androgen therapy, Prog Clin Biol Res 33:103, 1979.

10. Mohler J L, Gregory C W, Ford O H, 3rd, Kim D, Weaver C M, Petrusz P, Wilson E M, French F S: The androgen axis in recurrent prostate cancer. Clin Cancer Res 10(2):440, 2004.

11. Page S T, Lin D W, Mostaghel E A, Hess D L, True L D, Amory J K, Nelson P S, Matsumoto A M, Bremner W J: Persistent intraprostatic androgen concentrations after medical castration in healthy men. J Clin Endocrinol Metab 91(10):3850, 2006.

12. Liu J, Geller J, Albert J, Kirshner M: Acute effects of testicular and adrenal cortical blockade on protein synthesis and dihydrotestosterone content of human prostate tissue. J Clin Endocrinol Metab 61(1):129, 1985.

13. Labrie F: Adrenal androgens and intracrinology. Semin Reprod Med 22(4):299, 2004.

14. Titus M A, Gregory C W, Ford O H, 3rd, Schell M J, Maygarden S J, Mohler J L: Steroid 5alpha-reductase isozymes I and II in recurrent prostate cancer. Olin Cancer Res 11(12):4365, 2005.

15. Stanbrough M, Bubley G J, Ross K, Golub T R, Rubin M A, Penning T M, Febbo P G, Balk S P: Increased expression of genes converting adrenal androgens to testosterone in androgen-independent prostate cancer. Cancer Res 66(5):2815, 2006.

16. Nakamura Y, Suzuki T, Nakabayashi M, Endoh M, Sakamoto K, Mikami Y, Moriya T, Ito A, Takahashi S, Yamada S, Arai Y, Sasano H: In situ androgen producing enzymes in human prostate cancer. Endocr Relat Cancer 12(1):101, 2005.

17. El-Alfy M, Luu-The V, Huang X F, Berger L, Labrie F, Pelletier G: Localization of type 5 17beta-hydroxysteroid dehydrogenase, 3beta-hydroxysteroid dehydrogenase, and androgen receptor in the human prostate by in situ hybridization and immunocytochemistry. Endocrinology 140(3):1481, 1999.

18. Zaleska M, Bodek G, Jana B, Hansel W, Ziecik A J: Targeted destruction of normal and cancer cells through lutropin/choriogonadotropin receptors using Hecate-betaCG conjugate. Exp Olin Endocrinol Diabetes 111(3):146, 2003.

19. Dirnhofer S, Berger C, Hermann M, Steiner G, Madersbacher S, Berger P: Coexpression of gonadotropic hormones and their corresponding FSH and LH/CG-receptors in the human prostate. Prostate 35(3):212, 1998.

20. Tao Y X, Bao S, Ackermann D M, Lei Z M, Rao C V: Expression of luteinizing hormone/human chorionic gonadotropin receptor gene in benign prostatic hyperplasia and in prostate carcinoma in humans. Biol Reprod 56(1):67, 1997.

21. Emons G, Ortmann O, Pahw G S, Hackenberg R, Oberheuser F, Schulz K D: Intracellular actions of gonadotropic and peptide hormones and the therapeutic value of GnRH-agonists in ovarian cancer. Acta Obstet Gynecol Scand Suppl 155:31, 1992.

22. Lojun S, Bao S, Lei Z M, Rao C V: Presence of functional luteinizing hormone/chorionic gonadotropin (hCG) receptors in human breast cell lines: implications supporting the premise that hCG protects women against breast cancer. Biol Reprod 57(5):1202, 1997.

23. Lin J, Lei Z M, Lojun S, Rao C V, Satyaswaroop P G, Day T G: Increased expression of luteinizing hormone/human chorionic gonadotropin receptor gene in human endometrial carcinomas. J Olin Endocrinol Metab 79(5):1483, 1994.

24. Bodek G, Kowalczyk A, Waclawik A, Huhtaniemi I, Ziecik A J: Targeted ablation of prostate carcinoma cells through LH receptor using Hecate-CGbeta conjugate: functional characteristic and molecular mechanism of cell death pathway. Exp Biol. Med (Maywood) 230(6):421, 2005.

25. Hansel W, Leuschner C, Gawronska B, Enright F: Targeted destruction of prostate cancer cells and xenografts by lytic peptide-betaLH conjugates. Reprod Biol 1(1):20, 2001.

26. Leuschner C, Enright F M, Melrose P A, Hansel W: Targeted destruction of androgen-sensitive and -insensitive prostate cancer cells and xenografts through luteinizing hormone receptors. Prostate 46(2):116, 2001.

27. Ang J E, Olmos D, de Bono J S: CYP17 blockade by abiraterone: further evidence for frequent continued hormone-dependence in castration-resistant prostate cancer. Br J Cancer 100(5):671, 2009.

28. Tran C, Ouk S, Clegg N J, Chen Y, Watson P A, Arora V, Wongvipat J, Smith-Jones P M, Yoo D, Kwon A, Wasielewska T, Welsbie D, Chen C D, Higano C S, Beer T M, Hung D T, Scher H I, Jung M E, Sawyers C L: Development of a second-generation antiandrogen for treatment of advanced prostate cancer. Science 324(5928):787, 2009.

29. Simoni M, Gromoll J and Nieschlag E. The follicle-stimulating hormone receptor: biochemistry, molecular biology, physiology, and pathophysiology. Endocr Rev, 18: 739-773, 1997.

30. Goebelsmann U, Horton R, Mestman J H et al. Male pseudohermaphroditism due to testicular 17-hydroxysteroid dehydrogenase deficiency. J Olin Endocrinol Metab, 36: 867-879, 1973.

31. Scott J Z, Stanczyk F Z, Goebelsmann U and Mishell D R. A double-antibody radioimmunoassay for serum progesterone using progesterone-3-(O-carboxymethyl) oximino-[125I]-iodo-histamine as radioligand. Steroids, 31: 393-405, 1978.

32. Serafini P, Ablan F and Lobo R A. 5 alpha-Reductase activity in the genital skin of hirsute women. J Olin Endocrinol Metab, 60: 349-355, 1985.

33. Schally A V, Comaru-Schally A M, Nagy A et al. Hypothalamic hormones and cancer. Front Neuroendocrinol, 22: 248-291, 2001.

34. Ascoli M, Fanelli F and Segaloff D L. The lutropin/choriogonadotropin receptor, a 2002 perspective. Endocr Rev, 23: 141-174, 2002.

35. Stocco D M. StAR protein and the regulation of steroid hormone biosynthesis. Annu Rev Physiol, 63: 193-213, 2001.

36. Tremblay J J, Hamel F and Viger R S. Protein kinase A-dependent cooperation between GATA and CCAAT/enhancer-binding protein transcription factors regulates steroidogenic acute regulatory protein promoter activity. Endocrinology, 143: 3935-3945, 2002.

All publications cited herein are incorporated by reference in their entirety.

What is claimed is:

1. A method of decreasing steroidogenesis in prostate cancer cells, comprising:
disrupting the LH/LHR signaling pathway of a prostate cancer cell in a dose-dependent and time-dependent manner,
wherein said disrupting is accomplished by administering to the prostate cancer cells a LH receptor inhibitor that binds, couples to either of the LH or the LH receptor; or otherwise blocks the interaction between LH and LHR so as to prevent said cells from going into a castration resistant state, and wherein said inhibitor is selected from the group consisting of antibodies and small molecules.

2. The method of claim 1, wherein the prostate cancer cells are in a patient in need of decreasing the steroidogenesis in prostate cancer cells, and said disruption of the LH/LHR pathway in the prostate cancer cells is accomplished by administering to the patient an effective amount of an LH receptor inhibitor in a dose-dependent manner.

3. The method of claim 2, wherein the LH receptor inhibitor is administered externally to the prostate cancer cells.

4. The method of claim 2, wherein the prostate cancer cells are cultured in vitro, and the LH receptor inhibitor binds, couples to or otherwise blocks the LH Receptors on the prostate cancer cells from reacting with LH.

5. The method of claim 4, wherein the LH receptor inhibitor is selected from the group consisting of antibodies and small molecules.

6. The method of claim 2, wherein the LH receptor inhibitor binds, couples to or otherwise is operably linked to the LH such that the LH cannot activate the LH receptor.

7. The method of claim 6, wherein the LH receptor inhibitor is an antibody.

\* \* \* \* \*